United States Patent [19]

Smith et al.

[11] Patent Number: 4,974,461
[45] Date of Patent: Dec. 4, 1990

[54] ANTHROPOMORPHIC CARDIAC ULTRASOUND PHANTOM

[75] Inventors: Stephen W. Smith, Rockville; Jean E. Rinaldi, Silver Spring, both of Md.

[73] Assignee: The United States of America as represented by Department of Health and Human Services, Washington, D.C.

[21] Appl. No.: 432,433

[22] Filed: Nov. 6, 1989

Related U.S. Application Data

[62] Division of Ser. No. 257,174, Oct. 13, 1988, Pat. No. 4,894,013.

[51] Int. Cl.$^5$ .................. G01M 19/00; G09B 23/28
[52] U.S. Cl. ............................. 73/865.6; 73/1 DV; 434/268
[58] Field of Search ............. 73/866.4, 865.6, 865.9, 73/1 R, 1 DV, 3; 434/262, 267, 268, 272; 364/510; 600/16, 17; 128/653 R, 660.01, 661.08, 661.09, 661.1, 662.01

[56] References Cited

U.S. PATENT DOCUMENTS

| | | | |
|---|---|---|---|
| 3,208,448 | 9/1965 | Woodward | 600/17 |
| 3,597,766 | 10/1971 | Buck | 600/16 X |
| 4,277,367 | 7/1981 | Madsen et al. | 73/60 U X |

FOREIGN PATENT DOCUMENTS

685294  9/1979  U.S.S.R. ................... 73/866.4

OTHER PUBLICATIONS

H. Reul, "Cardiovascular Simulation Models", Life Support System 2, 77-98 (1984).
Hoeks et al, "Methods to Evaluate the Sample Volume of Pulsed Doppler Systems Ultrasound in Medicine and Biology", (1984), pp. 427-434; vol. 10, No. 4.
Van Citters et al, "Artificial Heart and Assist Devices: Directions, Needs, C Societal and Ethical Issues, Artificial Organs", 9(4), 375-415 (1985).
Altieri et al, "Implanatable Ventricular Assist Systems", *Artificial Organs*, 237-246 (1987).
Boote et al, "Performance Tests of Doppler Ultrasound Equipment with a Tissue and Blood Mimicking Phantom", *Journal of Ultrasound Medicine*, 7, 137-147 (1988).
Madsen et al, "Ultrasonically Tissue-Mimicking Liver Including the Frequency Dependence of Backscatter", *Med. Phys.* 9(5), 703-710 (1982) (part of p. 704 missing).
McKicken, "A Versatile Test-Object for the Calibration of Ultrasonic Doppler Flow Instruments", Ultrasound in Medicine and Biology, 12:245 (1986).
Walker et al, "Evaulating Doppler Devices Using a String Target", *Journal of Clinical Ultrasound* 10:25 (1982).
Newhouse et al, "A Proposed Standard Target for Ultrasound Doppler Gain Calibration", Ultrasound in Medicine and Biology, 8:313-316 (1982).

*Primary Examiner*—Tom Noland
*Attorney, Agent, or Firm*—Lowe, Price, LeBlanc, Becker & Shur

[57] ABSTRACT

Apparatus and method are disclosed for producing ultrasound readings of simulated blood flow through a model left ventricle or larger portion of the human heart, held inside a fluid filled chamber with membrane-covered windows, and through mitral and aortic valves cooperating therewith to provide a simulated human circulation flow free of reverberation artifacts and the like. Adjustable flow of a selected hydraulic fluid into and out of the chamber that also contains a plurality of ultrasound absorbing elements disposed oppositely to the ultrasound viewing windows is utilized to produce ultrasound signals picked up by an ultrasound transducer for processing in any known manner. A range of flow rate and systolic characteristics of a heart are readily simulated, to provide outputs substantially free of reverberations and ultrasound reflections from the inside walls of the chamber as well as the ultrasound absorbing elements.

6 Claims, 2 Drawing Sheets

ANTHROPOMORPHIC CARDIAC ULTRASOUND PHANTOM

This application is a division of application Ser. No. 07/257,174 filed Oct. 13, 1988 and now U.S. Pat. No. 4,894,013.

FIELD OF THE INVENTION

The present invention relates generally to ultrasound imaging and Doppler ultrasound devices, including continuous wave Doppler, pulsed Doppler, duplex Doppler/imaging systems and color-flow Doppler and methods for using them in cardiology, radiology, vascular surgery, obstetrics, neurology and other such applications. More particularly, this invention relates to test objects or phantoms for assessing the performance of ultrasound imaging and Doppler instruments in routine quality assurance measurements, acceptance testing of new devices and in training programs for clinical users of the equipment.

BACKGROUND OF THE PRIOR ART

Several Doppler phantoms have been described in the prior art. These fall into two main categories.

In the first group are phantoms which include a moving target such as a ball bearing or suspended string. The moving target is used to map the location and size of the sensitive Doppler sample volume of the ultrasound device. In this category, for example, Walker et al, "Evaluating Doppler Devices Using a String Target", *Journal of Clinical Ultrasound*, 10:25, 1982, describe a method in which a pair of moving strings at two different depths is used in a test target to measure Doppler sample volume size, sample location, and amplitude sensitivity to Doppler shift. An alternative method, described by Hoeks et al, "Methods to Evaluate the Sample Volume of Pulsed Doppler Systems", *Ultrasound in Medicine and Biology*, 10:427, 1984, is to couple a small target such as a sphere to a vibrating loudspeaker and then map the Doppler sample volume using this moving target.

In the second category of Doppler phantoms, the objective is to simulate blood flow, using a blood-mimicking liquid, through a simulated blood vessel in a tissue-mimicking material. Phantoms of this kind typically consist more or less of a solid block of tissue-mimicking material, such as gelatin or polymer, which contain tubes of varying diameters and bifurcations. Such phantoms seek to simulate blood flow through abdominal and peripheral vessels. Examples of such devices, of varying degrees of sophistication, are taught by Newhouse et al, "A Proposed Standard Target for Ultrasound Doppler Gain Calibration", *Ultrasound in Medicine and Biology*, 8, 313—1982; McDicken, "A Versatile Test-Object for the Calibration of Ultrasonic Doppler Flow Instruments", *Ultrasound in Medicine and Biology*, 12:245, 1986; and Boote et al, "Performance Tests of Doppler Ultrasound Equipment with a Tissue and Blood Mimicking Phantom", *Journal of Ultrasound Medicine*, 7, 137-147, 1988. phantoms allow independent measurement of "blood" flow and enable calibration of the fluid velocity estimations of Doppler ultrasound. Commercial versions of these test objects, "Tissue Mimicking Ultrasound Phantom" Model 409, Radiation Measurements, Inc., Middleton, Wis. 53362 (U.S. Pat. No. 4,277,367); "Ultrasound Doppler Phantom", ATS Laboratories, Inc., Bridgeport, Conn. 06608; and "Ultrasound Doppler Phantom", Interspec, Inc., Lewiston, Pa. 17044, are also available.

The most extensive application of medical Doppler ultrasound, however, is in cardiac diagnosis. Doppler ultrasound is used to measure blood flow through cardiac valves and thus to estimate pressure drops across individual heart valves for detection of valve dysfunctions. In addition, cardiac Doppler ultrasound is used to detect anatomical anomalies such as ventricular septal defects. The field of cardiac ultrasound imaging and Doppler ultrasound has a known and long-standing need for an anthropomorphic cardiac Doppler phantom to assess the performance of Doppler ultrasound under more realistic clinical conditions. Limited attempts to develop a Doppler phantom for cardiac applications include a modified cardiac pulse duplicator, "Cardiac Pulse Duplicator", Model MP1, Dynatek Laboratories, Annandale, N.J. 08801 as described by Cary et al in a private communication. However, this device is fabricated from rigid plastic, which generates strong acoustic reverberations unsuitable for diagnostic ultrasound examinations. In addition, such a modified pulse duplicator shows no similarity to the contracting muscular heart of human anatomy. Other examples include a modified cardiac pulse duplicator, "Valve Visualization Pulse Duplicator", Model MV/T1 Dynatek Laboratories, Annandale, N.J. 08801, as described by Gels et al, "In Vitro Ultrasound Flow Imaging Through Prosthetic Heart Valves", *Medical Instrumentation*, 21(2), 66-74, 1987, that includes a soft rubber vessel to simulate the aorta downstream of the aortic valve. This system, using microbubbles in tap water as an ultrasound contrast agent, enables flow visualization with diagnostic ultrasound imaging equipment to evaluate, qualitatively, the performance of prosthetic heart valves in vitro but does not permit simulation of the contracting heart of human anatomy.

In addition, Reul, "Cardiovascular Simulation Models", *Life Support Systems*, 2, 77-98, 1984, has developed hydraulically driven cardiovascular simulation models for the evaluation of prosthetic heart valves, using pressure transducers, flow transducers, and optical video filming of suspended particles in an aqueous-glycerol solution, but the cardiac models themselves are housed in rigid polymethylmethacrylate boxes. There are no viewing ports in the containers for ultrasound imaging or ultrasound Doppler studies. The polymethylmethacrylate containers produce high attenuation and reverberations that are unsuitable for ultrasound imaging or ultrasound Doppler studies. The hydraulic drive unit is mounted below the left ventricle in this device and precludes an apical ultrasound view, one of the most common views in clinical cardiac diagnosis. The hydraulic medium surrounding the left ventricle also is not specified. However, the attenuation scattering and velocity values of this medium are critical to the development of an ultrasound phantom as will be described below. Ordinary or distilled water, for example, is not suitable.

The field of cardiac assist devices, furthermore, includes left ventricular assist devices (LVAD) that typically have pneumatic pumps composed of a rigid plastic shell surrounding the flexible polymer left ventricle, Van Citters et al, "Artificial Heart and Assist Devices: Directions, Needs, Costs, Societal and Ethical Issues," *Artificial Organs*, 9(4), 375-415, 1985. The presence of air around the blood sac and the hard plastic shell make this technology unsuitable for a cardiac ultrasound phantom. One hydraulically driven LVAD is known which also consists of a rigid case surrounding the left ventricle, Altieri et al, "Implantable Ventricular Assist Systems", *Artificial Organs*, 11(3), 237–246, 1987. Again, however, this shell precludes use of the LVAD as an ultrasound phantom.

A need clearly exists in the art of Doppler and ultrasound imaging and the like for medical purposes for an anthropomorphic ultrasound phantom that realistically enables ultrasound analyses of simulated defects in human hearts and provides reverberation free outputs suitable for comparison of different devices and simulation studies.

SUMMARY OF THE INVENTION

A principal object of this invention is to provide an apparatus to simulate the human cardiac anatomy for medical applications such as the testing of ultrasound imaging, ultrasound Doppler or color-flow Doppler imaging devices.

Another object of this invention is to provide a novel phantom apparatus in which an ultrasound contrast medium is circulated within a circulatory loop to simulate human cardiac blood circulation that can be subjected to ultrasound viewing with minimal reverberation.

In another aspect of this invention, a primary object is to provide a method for intramural comparisons or testing against a reference of ultrasound imaging, ultrasound Doppler or color-flow Doppler imaging devices.

These and other related objects of the present invention are realized in a preferred embodiment of an apparatus comprising first means for simulating a flexible portion of a human heart, comprising valve means for controlling inflow to and outflow therefrom;

pressurizing chamber means for substantially surrounding said first means, said chamber means having a drain and a hydraulic fluid flow port and also having a first ultrasound viewing window in a first chamber wall located at a selected distance from said first means;

reservoir means for holding a quantity of a blood analog fluid and communicating with said valve means to form a closed loop blood-analog fluid flow circuit with said first means; and hydraulic flow means for providing a controlled flow of a pressurized hydraulic fluid into and out of said chamber outside of said first means to pressurize said first means and drive a corresponding blood-analog fluid flow therethrough.

In another aspect of this invention, a preferred embodiment of the method of this invention comprises the steps of forming a closed recirculating flow of a blood analog fluid through a mitral valve and an aortic valve of a flexible portion of a simulated human heart;

surrounding a substantial portion of said flexible portion with a hydraulic fluid contained within a chamber provided with a window for ultrasound viewing of said flexible portion therethrough;

controlling a pressure of said hydraulic fluid to correspondingly pressurize said flexible portion to thereby generate a flow of said blood-analog fluid therethrough via said mitral and aortic valves; and ultrasonically viewing said flexible portion via said viewing window to generate data corresponding to an image and Doppler signals related to said blood-analog flow therethrough.

These and other objects and advantages of the present invention will become more apparent in view of the following detailed description when understood with reference to the drawing.

DETAILED DESCRIPTION OF THE DRAWING

DESCRIPTION OF THE PREFERRED EMBODIMENTS

Figure 1:
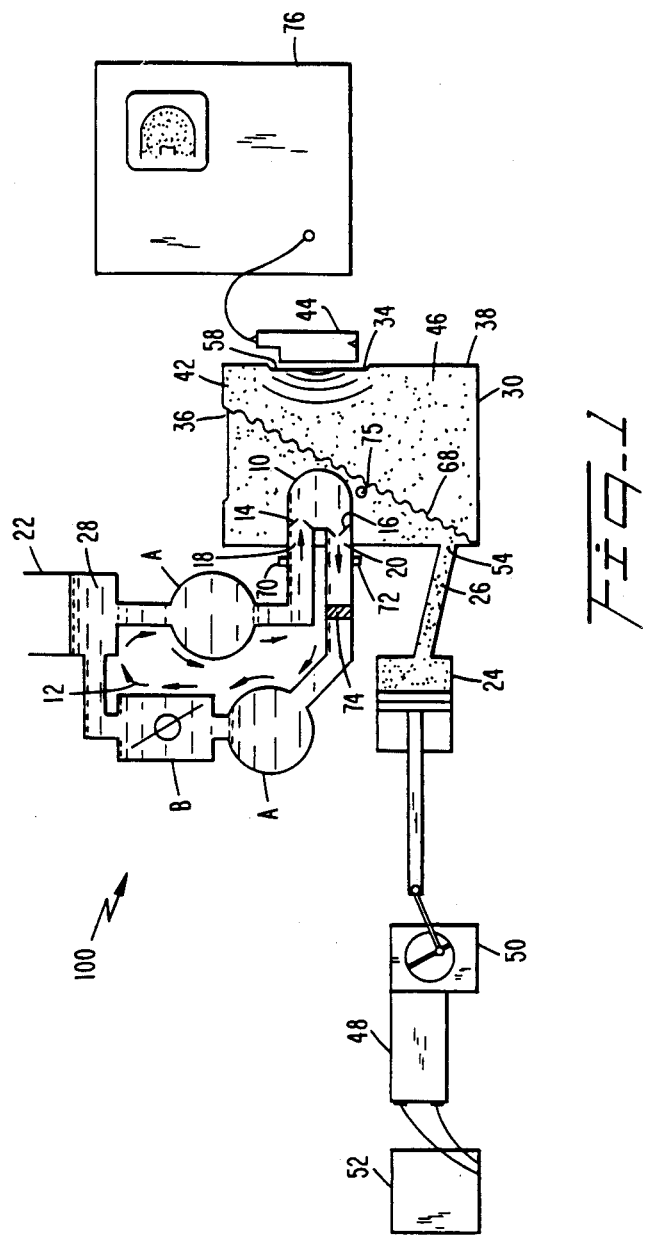
FIG. 1 illustrates a schematic view, in partial cross-section, of a preferred embodiment of the phantom according to the apparatus of this invention.

FIG. 1 is a partially sectioned schematic view of a phantom 100 according to a preferred embodiment of the apparatus of this invention. A flexible left ventricular sac 10 ("left ventricle", hereinafter, for simplicity), conveniently fabricated of a durable, flexible polymer or plastics material according to a typical geometry of an artificial left ventricle, is connected to a simulated circulatory loop 12. The left ventricle 10 includes mechanical prosthetic heart valves 14 (mitral) and 16 (aortic) at mitral and aortic ports 18 and 20, respectively.

The simulated circulatory loop 12 also includes a reservoir 22 and assorted mechanical features, as described more fully hereinbelow, to incorporate the compliance and resistance to blood flow typical of the human vascular system. Such features include two variable compliance chambers (A) and a variable resistance manifold (B). The reservoir 22 and simulated circulatory system 12 contain a blood analog, i.e., blood-mimicking, fluid 28 which also serves as an ultrasound contrast medium.

A suitable blood surrogate or blood-mimicking fluid of this type has been described by Boote et al, supra, and consists of 30 um polystyrene spheres in a glycerol-aqueous solution. Alternatively, to provide a high contrast agent and thus to enable achievement of a higher signal-to-noise ratio in the ultrasound imaging/Doppler measurements, microbubbles suspended in an aerated glycerol-water solution can be introduced by a stirrer or bubbler of known type (not shown) in reservoir 22.

A flow visualization chamber 30 ("chamber", hereinafter) surrounds the left ventricle 10 and is conveniently constructed of a rigid plastic material, e.g., polymethylmethacrylate. Three membrane-covered windows 32, 34 and 36 are provided at mutually orthogonal chamber walls 38, 40 and 42, respectively, to enable ultrasonic imaging/Doppler examinations of the left ventricle 10 and prosthetic valves 14 and 16 from the three conventional cardiac ultrasound views, i.e., the long axis (LA), short axis (SA) and apical (AP), as indicated by arrows so identified in FIG. 2. An ultrasound transducer 44 is shown in FIG. 1 positioned over one of the windows of chamber 30.

Chamber 30 is filled with a hydraulic fluid 46 which allows ultrasound viewing of ventricle 10 and which also mimics properties of human tissue as related to variables of ultrasound propagation velocity and attenuation. Various such fluids are known and have been extensively utilized in the prior art. Mineral oil and silicone fluid are included among such fluids and both possess the additional desirable feature that they are optically transparent. Degassed, distilled water simulates the transmission velocity of human tissue fairly closely, but shows no significant ultrasound attenuation. Gaseous water, e.g., distilled or tap water which contains bubbles, strongly scatters ultrasound and thus tends to attenuate and obscure the ultrasound signals coming from within the simulated left ventricle 10 in a device using the same. Yet another alternative having certain advantageous properties as a tissue-mimicking hydraulic fluid is a slurry of agar gel and graphite scatterers which also mimics ultrasound backscatter as well as velocity and attenuation comparable to those of human tissue but, unfortunately, this slurry has the disadvantage that it is optically opaque. One version of such a tissue-mimicking slurry is described by Madsen et al, "Ultrasonically Tissue Mimicking Liver Including the Frequency Dependence of Backscatter", *Medical Physics*, 9(5), 703–710, 1982.

An adjustable delivery pump such as a variable speed piston pump 24 driven by a variable speed DC motor 48 via an adjustable stroke drive 50 of known type, e.g., one with a cam or crank adjustable for varying the entire stroke and % of forward and reverse stroke time periods, receives power from a conventional power supply 52. Pump 24 is connected to the viewing chamber 30 by a single port 54 by a length of compressible tubing 26 which allows fine adjustments to the pump flow output.

With this arrangement, as the hydraulic fluid 46 is pumped in and out of chamber 30 by to-and-fro motion of the piston of pump 24, the left ventricle 10 is forced to pump the ultrasound contrast medium 28, i.e., the blood analog fluid, through circulatory loop 12. Note that this is made possible because when pump 24 drives hydraulic fluid 46 into chamber 30 mitral valve 14 will close and only aortic valve 16 will permit flow therethrough of blood analog fluid 28. On the other hand, when piston pump 24 withdraws some of the hydraulic fluid 46 from chamber 30, due to the hydrostatic head provided by reservoir 22 located vertically above chamber 30, blood analog fluid 28 will flow through then open mitral valve 14 into left ventricle 10 and, at this time, aortic valve 16 will close up. The consequence of the action of piston pump 24, therefore, is to generate pulsatile flow of blood analog fluid 28 around circulatory loop 12 by action of left ventricle 10 and mitral and aortic valves 14 and 16, respectively. It is this simulated action of the human circulatory system that may advantageously be viewed in any of the three principal directions, LA, SA or AP (as defined hereinabove) by appropriate location of transducer 44 at a corresponding viewing window.

As persons skilled in the mechanical arts will appreciate, the simulated systolic and diastolic durations of the flow in circulatory loop 12 may be readily controlled by changing the shape of the cam. The voltage or speed of motor controls the beat rate, and the length of the shaft determines the stroke volume. The systolic and diastolic durations of the flow of the loop 12 can also be controlled by adjusting and regulating the speed of pump motor 48 and/or the adjustable stroke drive 50 driving the piston (not numbered) in piston pump 24 as well as externally applied compression, by any known means, of tube 26.

Figure 2:
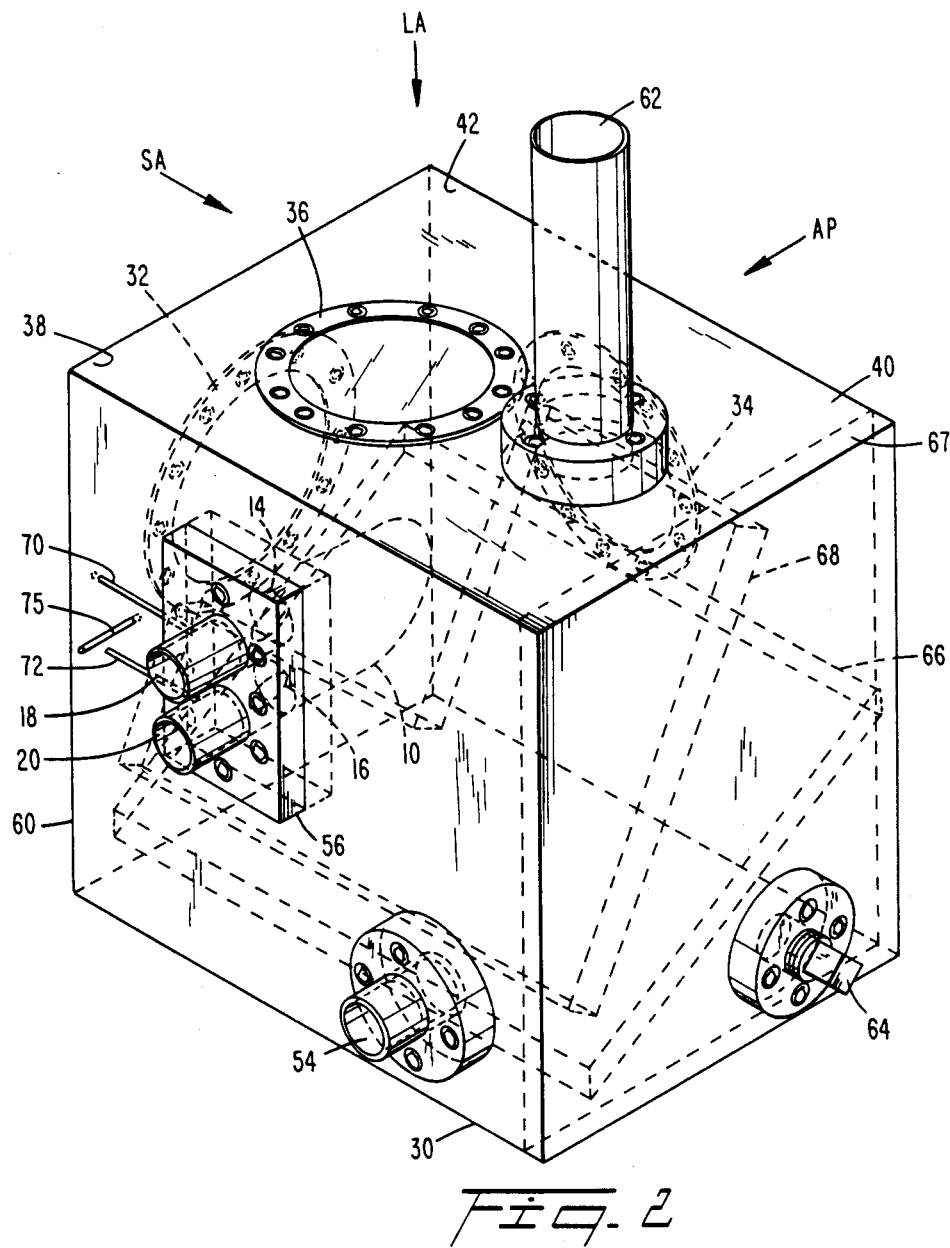
FIG. 2 is a partial perspective view illustrating details of a flow visualization chamber containing a simulated left ventricle in a phantom according to a preferred embodiment of the apparatus of this invention.

FIG. 2 is a partial perspective view illustrating details of a prototype flow visualization chamber 30 according to a preferred embodiment of this invention and contains the left ventricle 10 as described hereinabove. In this operating laboratory prototype, left ventricle 10 is suspended in the back wall of chamber 30 at about the level of prosthetic mitral and aortic valves 14 and 16, respectively, by a pressure plate 56 sealed to chamber 30 by any known means, e.g., "O" rings (not shown). In this prototype chamber 30, because it was designed for simulated experimental studies on an adult human heart, the dimensions of chamber 30 were selected to be 7"×9"×9" for the base and 9" for the height. The left ventricle 10 is positioned in chamber 30 approximately 3" from the chamber walls, as this dimension is believed to be a reasonable approximation for the depth of an adult human's heart from his or her chest walls. The mitral inflow port 18 and the aortic flow port 20 are disposed in the prototype as illustrated in FIG. 2. Viewing ports 32, 34, and 36 in the corresponding walls of the generally cubically shaped viewing chamber of the prototype are mounted in 3"- and 4"-inch diameter aluminum rings (not numbered) which are large enough to easily accommodate conventional ultrasound transducers of known type. Flexible membranes are provided in each of the viewing ports and, referring to FIG. 1, such a membrane 58 is shown in vertical section in window 34.

The membrane in each of the viewing ports of the prototype consists of a 0.003" thick flexible sheet, preferably of a polyester or plastics material, which is strong enough to accommodate the expected hydrostatic pressures in the chamber during hydraulic pumping operation thereof. A piston pump 48 is connected at a back wall 60 of chamber 30 at port 54. A vertical fill and overflow pipe 62, conveniently located at the uppermost portion of chamber 30 is sealed during operation of the phantom. A hydraulic fluid drain 64 is provided close to the bottom of chamber 30, conveniently at a side wall of the chamber.

A plurality of acoustic absorbers, such as 66 and 68, are mounted inside chamber 30 at selected angles from the vertical, and are located to be oriented generally opposite to a corresponding one of the viewing windows 36, 32 and 34, respectively. These acoustic absorbers, such as 66, 67 are very important in the present invention as they absorb most of the transmitted ultrasound energy to prevent reverberation artifacts in the ultrasound images and Doppler signals. These acoustic absorbers 66, 67 and 68 may preferably be fabricated from flexible rubber materials such as butyl rubber which closely matches the acoustic impedance of human tissue, so as to minimize ultrasound reflections from the inside surfaces of the walls and the outside surfaces of the absorbers themselves.

Experimental results show optimum performance of the phantom is obtained when acoustic absorbers 66 and 68 are respectively inclined at about 30° to the planes of viewing windows 36 and 34, respectively. Acoustic absorber 67 is provided an aperture to allow drainage to drain 64 and is preferably placed adjacent the wall opposite window 32 to accommodate the other two acoustic absorbers as illustrated in FIG. 2. Persons skilled in the art will readily conceive of ways to incline and integrate the three acoustic absorbers so that each is at about 30° to the plane of a corresponding window opposite. In practice, because the absorbent material is soft, a layer thereof is adhered to a thin sheet of transparent stiff plastic and the latter glued in place in chamber 30 as desired.

Several commercial versions of such acoustic absorbers are available, e.g., as marketed by B. F. Goodrich, Rho-C Rubber, and Diasonics, Inc. Soab.

During the operation of the cardiac phantom 10, formed as described hereinabove, cross-sectional ultrasound images of the beating left ventricle 10 show flow patterns of the contrast medium, e.g., aerated tap water or other selected blood analog fluid, as it flows through the mitral and aortic valves 14 and 16, respectively, and along the walls of the left ventricle 10. Ultrasound Doppler signals of this type can be readily interpreted in known manner and with known apparatus, can be utilized to obtain quantitative values of fluid (i.e., blood) velocities. Color-flow Doppler images may also be developed in known manner from the ultrasound data picked up by ultrasound transducer 44, as described hereinabove, to further define the flow profiles in left ventricle 10.

First and second pressure catheters 70 and 72 are mounted upstream and downstream, respectively, of the mitral and aortic prosthetic valves 14 and 16 and may be used to make direct measurements of pressure drops across the corresponding valves and, thus, to enable calibration and quality assurance validation of related Doppler flow measurements. A third catheter 75 is provided in a wall of chamber 30 to enable pressure readouts of hydraulic fluid 46 therein, this pressure being in correspondence with the pressure in the left ventricle 10. An invasive electromagnetic flowmeter 74 may be located in the circulatory loop, as indicated in FIG. 1, and may be utilized to further calibrate Doppler flow measurements.

Any known means 76, comprising typically an ultrasound scanner data display, a data recorder and a data processor, of the type commonly found in any modern medical facility, may be used with the phantom in conventional manner to utilize the data therefrom.

Stenotic valves or bio-prosthetic valves may also be utilized with left ventricle 10 in alternative embodiments of this invention.

Pinholes or other selected defects may be introduced in replaceable valve leaflets (not shown) at valves 14 and 16 to produce fluid jets and may be advantageously used to simulate partially damaged heart valve conditions. Double ventricle or four-chambered simulated hearts may also be included instead of the solitary left ventricle 10, with associated septal defects to simulate other anatomic anomalies. Persons skilled in the art will appreciate that rather straightforward and easily managed changes in the appropriate connections to circulatory loop 12 would be necessary as more sophisticated and multichambered simulated hearts are so utilized.

A separate embodiment of the invention provides an alternate implementation of the phantom which provides simulation of the improved human tissue and the human torso by using a solid cylinder made of a tissue mimicking material such as a gelatin, polymer or plastic, among other materials. The tissue mimicking material contains scatterers of approximately 20–100um in diameter such as plastic or graphite scatters. Such material mimics the attenuation, velocity and ultrasound image texture of human tissue and has been described by Smith et al, below and Madsen et al, below. Within the solid cylinder a cavity is molded which contains, e.g., the flexible left ventricle, prosthetic heart valves and the tubes which carry the blood analog fluid to the external circulation. The cavity is large enough to also contain a layer, e.g., a surrounding layer, of hydraulic fluid which is connected to the piston pump by a single port molded into the cylinder. Thus, the same hydraulic pumping mechanism described above can be used. However, other suitable mechanisms may also be utilized. The use of a tissue-mimicking cylinder removes the need for individual ultrasound viewing ports and the internal acoustic absorbing layers since the entire surface of the tissue-mimicking cylinder is now acoustically transparent. The material thus matches the attenuating properties of tissue and thus prevents reverberation artifacts (Madsen EL, Zagzebski JA, Banjavic RA, et al: Tissue mimicking materials for ultrasound phantoms. Med Phys 5:391, 1978), the entire content of which is incorporated herein by reference. (Smith, S. W., Lopez, H. and Bodine, W. J., "Frequency Independent Contrast-Detail Analysis", Ultrasound in Medicine and Biology, 11, 467–477, 1985, the entire content of which is incorporated herein by reference).

Another alternate embodiment of the invention substitutes a constant vacuum source, such as that created by a Venturi tube, to draw the blood analog fluid around the circulatory system. Prosthetic valves electrically driven by solenoids may be opened and closed with proper timing to pump the flexible left ventricle. This embodiment removes the need for the hydraulic pumping system.

It should be understood that the apparatus as described hereinabove is highly useful not only to study selected approximations to real-life heart defects but also, for a selected left ventricle 10 or simulated heart, for intramural comparisons of a number of ultrasound devices, e.g., for quality control at the end of a production line of a particular model of such devices for comparing them against an established standard or, in the alternative, for comparing devices from a number of different sources to determine their relative performances. Obvious variations on these themes will no doubt occur to persons skilled in the art, especially after they develop a thorough understanding of the structure and the advantages to be obtained by the present invention.

In light of the possible uses discussed in the immediately preceding paragraph, at least two methods of using the type of apparatus hereindescribed are readily presented.

In a first example, for comparing a plurality of nominally similar devices to a reference to determine their acceptability for quality control purposes, a user may first select a suitable standard device such as particular left ventricle 10, a particular blood analog fluid 28, a particular hydraulic fluid 46 and a particular mode of operating the adjustable piston pump 24 to establish a reference operational cycle. Other parameters, e.g., the temperatures of the fluids and the ambient pressure may, likewise, be regulated or compensated for in known manner. The system may be started and operated for a suitable period of time until operational parameters such as pressures measured at catheters 70 and 72 and the appropriate flow rates as measured at flow meter 74 all attain steady state values to acceptable tolerances. One of the devices to be tested may then be successively connected to ultrasonic transducers such as 44 at one or more of the viewing windows 32, 34 or 36. The appropriate data so obtained may be collated and reduced in any known manner and the process repeated for the next device to be compared. Persons skilled in the art may thus soon establish acceptance criteria and the apparatus according to this invention may be utilized according to this method for quality control purposes.

In an alternative use, with the apparatus operated at acceptable steady state conditions for a particular left ventricle 10 (or a partial or complete surrogate for the human heart) data as described in the immediately preceding paragraph may be obtained and reduced for a known device being utilized as a reference. Each of any competing devices may then be similarly tested and the reduced data compared for an evaluation of the suitability of the nominally competing device as a possible substitute or superior replacement for the selected standard device.

A third alternate use is to train cardiac physicians and technologists in the use of ultrasound imaging and ultrasound Doppler equipment.

It should be understood that persons skilled-in the art, armed with the details of the preferred embodiments as disclosed herein, will find obvious substitutes for the various elements, e.g., any of a variety of known systolic or pulsatile output producing pumps in place of the piston pump 24 as discussed hereinabove, to advantageously practice the present invention. It should therefore further be understood that the preferred embodiments disclosed and discussed herein are intended to be merely illustrative in nature and not as limiting the scope of the present invention, which is defined by the claims appended hereinbelow.

What is claimed is:

1. A method of comparing ultrasound devices for imaging a selected simulated anthropomorphic cardiac flow, comprising forming a closed recirculating flow of a blood-analog fluid through a first valve means for controlling inflow and a second valve means for controlling outflow of a flexible portion of a simulated human heart;

surrounding a substantial portion of said flexible portion with a hydraulic fluid contained within a chamber provided with a means for ultrasound viewing of said flexible portion therethrough;

controlling the pressure of said hydraulic fluid to correspondingly pressurize said flexible portion to thereby generate a flow of said blood-analog fluid therethrough via said first and said second valve means;

ultrasonically viewing with a first of said ultrasound devices said flexible portion via said viewing means to generate data corresponding to an image related to said blood-analog flow therethrough;

repeating the preceding steps with a second one of said ultrasound devices; and comparing the data generated by said first and second devices.

2. The method of claim 1, wherein said first device is selected to be a reference device; and determining a quality of said second device from said data comparison between data generated by said reference device and said second device.

3. A method for generating an ultrasound image related to a simulated anthropomorphic cardiac flow, comprising forming a closed recirculating flow of a blood-analog fluid through a first valve means for controlling inflow and a second valve means for controlling outflow of a flexible portion of a simulated human heart;

surrounding a substantial portion of the flexible portion with a hydraulic fluid contained within a chamber provided with a means for ultrasound viewing of the flexible portion therethrough;

controlling the pressure of the hydraulic fluid to correspondingly pressurize the flexible portion to thereby generate a flow of the blood-analog fluid therethrough via the first and the second valve means;

absorbing any undesired ultrasound artifacts generated during the pressure controlling step by disposing an ultrasound absorbing element within the hydraulic fluid inside the chamber in a selected orientation and location therein; and ultrasonically viewing the flexible portion via the viewing means to generate data corresponding to an image related to the blood-analog flow therethrough.

4. The method of claim 3, wherein said ultrasonic viewing is conducted along the direction of a long axis of the simulated human heart.

5. The method of claim 3, wherein said ultrasonic viewing is conducted along the direction of a short axis of the simulated human heart.

6. The method of claim 3, wherein said ultrasonic viewing is conducted along an apical direction of the simulated human heart.

* * * * *